US00PP18539P2

(12) United States Plant Patent
Akerboom

(10) Patent No.: US PP18,539 P2
(45) Date of Patent: Mar. 4, 2008

(54) *ASTER* PLANT NAMED 'PRETTY WENDY'

(50) Latin Name: *Aster L.*
Varietal Denomination: Pretty Wendy

(75) Inventor: Petrus J. Akerboom, Ter Aar (NL)

(73) Assignee: De NachTVlinder B.V., Ter Aar (NL)

( * ) Notice: Subject to any disclaimer, the term of this patent is extended or adjusted under 35 U.S.C. 154(b) by 0 days.

(21) Appl. No.: 11/439,940

(22) Filed: May 24, 2006

(51) Int. Cl.
*A01H 5/00* (2006.01)

(52) U.S. Cl. ..... Plt./355

(58) Field of Classification Search ..... Plt./355
See application file for complete search history.

(56) References Cited

PUBLICATIONS

UPOV–ROM GTITM, Plant Variety Database, 2006/03 GTI Jouve Retrieval Software, citation for 'Pretty Wendy'. (1 page total).*

* cited by examiner

*Primary Examiner*—Kent Bell
*Assistant Examiner*—S. B. McCormick-Ewoldt

(57) ABSTRACT

A new and distinct *Aster* plant cultivar is disclosed, characterized by a narrowly elliptic leafshape, more than two whorls of ray florets and a pure white ray floret color.

1 Drawing Sheet

Latin name of the genus and species: *Aster L.*
Denomination: 'PRETTY WENDY'.

BACKGROUND OF THE INVENTION

The new cultivar 'PRETTY WENDY' is a product of a hybridization of the parent *Aster* plant varieties, Nachtvlinder B. V. selection numbers 99321×99117 (not patented). The new cultivar was discovered and selected by Nachtvlinder B. V., in Ter Aar, Holland in June 2002.

Asexual reproduction of the new cultivar 'PRETTY WENDY' by vegetative cuttings was performed in Ter Aar, Holland and has shown that the unique features of this new cultivar are stable and reproduced true to type on successive generations.

SUMMARY OF THE INVENTION

The cultivar 'PRETTY WENDY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PRETTY WENDY.' These characteristics in combination distinguish 'PRETTY WENDY' as a new and distinct *Aster* cultivar:

1. Narrowly elliptic leafshape;
2. More than two whorls of ray florets; and
3. Pure white ray floret color.

Plants of the new cultivar 'PRETTY WENDY' differ from the parent varieties in most horticultural characteristics, including leaf shape and plant form.

In comparison to the commercially available variety 'White Prestige' (not patented) the new variety is taller and has a more upright overall plant growth habit. Also, the new variety 'PRETTY WENDY' has brighter white ray florets and a more upright ray floret aspect. Also, the leaf shape of the new variety 'PRETTY WENDY' is linear compared to the elliptic leaf shape of 'White Prestige.' Finally, 'PRETTY WENDY' is less sensitive to Botrytis in flower than 'White Prestige' and less sensitive to powdery mildew.

BRIEF DESCRIPTION OF THE PHOTOGRAPH

The accompanying photograph in FIG. 1 illustrates in full color a typical plant of 'PRETTY WENDY' grown in a field. One cutting was used, planted in April and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PRETTY WENDY' plants grown in Ter Aar, Holland during the month of June 2005. The growing temperature ranged from 16° C. to 18° C. at night to 20° C. to 30° C. during the day. Measurements and numerical values represent averages of typical flowering types.

Botanical classification: *Aster* L. cultivar 'PRETTY WENDY.'
Commercial classification: Cut flower *Aster*.

PROPAGATION

Time to rooting: Total time is 13 weeks, with 7 weeks of 18 hours of daylight followed by 6 weeks of 12 hours of daylight.
Root description: Fine, fibrous.
Form: Narrow inverted triangle.
Growth habit: Upright.
Height: Approximately 66.2 cm.
Plant spread: Approximately 18.3 cm.
Growth rate: Moderate.
Branching characteristics: Free-branching.
Diameter of branches: Approximately 2 mm.

Average number of branches: Approximately 16.
Length of lateral branches: Approximately 18.7 cm.
Number of leaves per lateral branch: Approximately 12.
Stem color: Between Green 143A and Green 143B with lighter longitudinal stripes between Yellow-Green 144A and Yellow-Green 144B.
Age of plant described: Approximately 90 days.

FOLIAGE

Leaf:
*Arrangement.*—Alternate single.
*Average length.*—Approximately 10.4 cm.
*Average width.*—Approximately 1.3 cm.
*Shape of blade.*—Narrowly elliptic.
*Apex.*—Acute.
*Base.*—Cuneate.
*Margin.*—Outwardly entire, but in fact with very small serrated teeth with an average 30 teeth per cm. Lower leaves are serrate with an average 1 tooth per cm.
*Texture of top surface.*—Slightly glossy, smooth.
*Texture of bottom surface.*—Smooth.
*Leaf internode length.*—Approximately 2.6 cm.
*Color.*—Young foliage upper side: Near Green 137A. Young foliage under side: Between Green 137B and Green 137C. Mature foliage upper side: Between Green 137A and 139A. Mature foliage under side: Near Green 137B.
*Venation.*—Type: Palmately net. Venation color upper side: Near Yellow-Green 144A. Venation color under side: Near Green 143A.
Petiole: No petioles, leaves are sessile (decurrent).

BLOOM

Inflorescence:
*Flowering habit.*—Continuous, depending on method of culture. Terminal inflorescence opens first, all flowers have opened in about five weeks. Flower response time when grown as cut flower, average 13 weeks.
*Inflorescence form.*—Solitary heads.
*Natural flowering season.*—Late September to late October.
*Number of inflorescences per lateral branch.*—Approximately 10.
*Inflorescence diameter.*—Approximately 3 cm.
*Inflorescence depth.*—Approximately 1.8 cm.
*Inflorescence longevity on plant.*—Approximately 14 days.
*Persistence.*—Self-cleaning.
*Total disc diameter.*—Approximately 4 mm.
*Receptacle diameter.*—Approximately 1.4 cm.
*Receptacle height.*—Approximately 7 mm.
*Inflorescence aspect.*—Upright.
*Inflorescence shape.*—Inflorescences consisting of many rows of ray florets and a receptacle consisting of four rays of involucres.
*Fragrance.*—None detected.
Ray florets:
*Appearance.*—Matte.
*Texture.*—Smooth with very short hairs at the base near Yellow-White 158D.
*Average number of ray florets per inflorescence.*—135.
*Average number of rows of ray florets.*—Approximately 7.
*Shape.*—Oblanceolate.
*Aspect.*—Outward with centrally placed ray florets upright.
*Margin.*—Entire.
*Apex.*—Broad acute to slightly retuse.
*Base.*—Narrow attenuate.
*Arrangement.*—Rotate.
*Length.*—Approximately 1.5 cm.
*Width.*—Approximately 2.5 mm.
*Color.*—Upper surface at first opening: Near White 155B. Upper surface at maturity: Near White 155B. Upper surface at fading: Near Greyed-Orange 164D. Under surface at first opening: Near White 155B. Under surface at maturity: Near White 155B.
Disc florets:
*Appearance.*—Shiny.
*Texture.*—Smooth.
*Average number of florets per disc.*—Approximately 20.
*Shape.*—Tubular.
*Apex.*—Acute.
*Base.*—Fused into tubular shape.
*Arrangement.*—Rotate, spirally arranged.
*Average length.*—Approximately 5 mm.
*Average width.*—Approximately 0.3 mm.
*Color.*—At first opening: Near Green 137C. At maturity: Apex: Near Yellow-Green 150C and Green-Yellow 1C. Mid-Section: Between Yellow-Green 145B and Yellow-Green 145C. Base: Between Green 137C and Green 137D. At fading: Near Yellow-Green 152A to Grey-Brown 199A.
Peduncle:
*Length.*—At terminal end (shortest): Approximately 2.5 cm. At lateral end (longest): Approximately 6.9 cm.
*Angle to stem.*—30°.
*Strength.*—Strong.
*Color.*—Near Green 143A.
*Habit.*—Slightly upright.
*Diameter.*—Approximately 1 mm.
*Surface texture.*—Lightly pubescent.
Inflorescence bud:
*Length.*—Approximately 8 mm.
*Diameter.*—Approximately 1 cm.
*Form.*—Obovate.
*Color.*—Near Green 137A with apex between Yellow-Green 150A and Yellow-Green 150B.
Involucral bracts (Phyllaries):
*Appearance.*—Slightly glossy.
*Texture.*—Smooth.
*Number.*—Approximately 42.
*Shape.*—Linear, curved.
*Margin.*—Entire.
*Apex.*—Acute.
*Base.*—Cuneate.
*Arrangement.*—Rotate with an average of four rows.
*Length.*—Approximately 6 mm.
*Width.*—Approximately 1.5 mm.
*Color.*—Upper side: Near Green 137A. Under side: Near Green 137B.

REPRODUCTIVE ORGANS

Ray florets:
*Number of pistils per floret.*—1.
*Stigma shape.*—Decurrent.
*Stigma color.*—Near Yellow 8C.

*Style color.*—Between Yellow-Green 145C and Yellow-Green 145D.
*Style length.*—Approximately 2.5 mm.
*Stamens.*—Absent.

Disc florets:
*Number of pistils per floret.*—1.
*Stigma shape.*—Decurrent.
*Stigma color.*—Near Yellow 8C.
*Style color.*—Between Yellow-Green 145C and Yellow-Green 145D.
*Style length.*—Approximately 2.5 mm.
*Stamens.*—Absent.

OTHER CHARACTERISTICS

Disease resistance: Less sensitive to Botrytis in flower than 'White Prestige' and less sensitive to powdery mildew.

Drought tolerance/cold tolerance: Moderate. Need more details, example: Flowering plants are hardy to low temperatures about −15° C. and high temperatures of at least 35° C. with moderate wind and rain tolerance.

Fruit/seed production: Commercially, this plant is not used or observed in a stage where seeds would be produced. Therefore, seed production has not been observed.

What is claimed is:

1. A new and distinct cultivar of *Aster* plant named 'PRETTY WENDY' as herein illustrated and described.

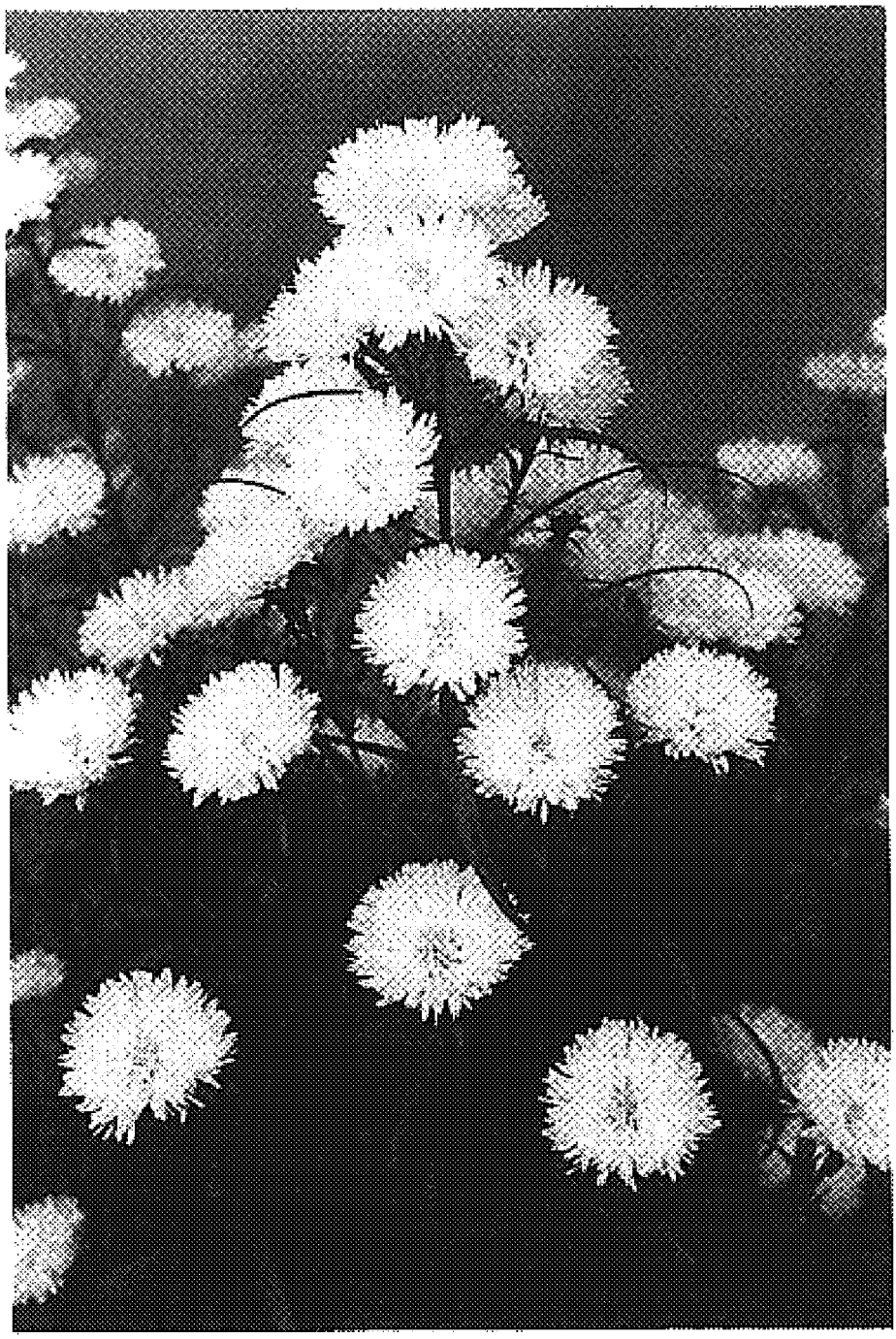

* * * * *